United States Patent [19]
Bachynsky

[11] Patent Number: 5,865,804
[45] Date of Patent: Feb. 2, 1999

[54] ROTARY CAM SYRINGE

[76] Inventor: Nicholas Bachynsky, 701 W. 14th St., Texarkana, Tex. 75501

[21] Appl. No.: 895,161

[22] Filed: Jul. 16, 1997

[51] Int. Cl.⁶ ....................................................... A61M 5/20
[52] U.S. Cl. ........................... 604/134; 604/131; 604/157; 604/233
[58] Field of Search ..................................... 604/131, 134, 604/135, 136, 156, 157, 173, 206, 211, 233, 151, 152, 154, 181, 187, 208, 209, 213, 227; 222/336, 327, 386

[56] References Cited

U.S. PATENT DOCUMENTS

| | | |
|---|---|---|
| 2,549,417 | 4/1951 | Brown . |
| 2,591,046 | 4/1952 | Brown . |
| 4,202,314 | 5/1980 | Smirnov et al. . |
| 4,214,584 | 7/1980 | Smirnov et al. . |
| 4,226,236 | 10/1980 | Genese . |
| 4,312,343 | 1/1982 | Leveen et al. . |
| 4,413,991 | 11/1983 | Schmitz et al. . |
| 4,529,403 | 7/1985 | Kamstra . |
| 4,583,974 | 4/1986 | Kokernak . |
| 4,613,326 | 9/1986 | Szwarc . |
| 4,792,329 | 12/1988 | Schreuder . |
| 4,874,381 | 10/1989 | Vetter . |
| 4,898,580 | 2/1990 | Crowley . |
| 4,968,299 | 11/1990 | Ahlstrand et al. . |
| 4,978,339 | 12/1990 | Labouze et al. . |
| 4,983,164 | 1/1991 | Hook et al. . |
| 4,994,043 | 2/1991 | Ysebaert . |
| 5,041,088 | 8/1991 | Ritson et al. . |
| 5,080,649 | 1/1992 | Vetter . |
| 5,267,963 | 12/1993 | Bachynsky ............................. 604/134 |
| 5,273,544 | 12/1993 | Van Der Wal . |
| 5,395,326 | 3/1995 | Haber et al. . |
| 5,423,752 | 6/1995 | Haber et al. . |

FOREIGN PATENT DOCUMENTS 0072057  2/1983  European Pat. Off. .

OTHER PUBLICATIONS

Hamilton, James G., *The Journal of Family Practice*, vol. 41, No. 2 (Aug.), 1995, pp. 169–175.
Ippolito, Giuseppe et al., *JAMA*, Aug. 24/31, 1994, vol. 272, No. 8, pp. 607–610.
Tereskerz, Patricia M. et al., *The New England Journal of Medicine*, "Occupational Exposure To Blood Among Medical Students", Oct. 10, 1996, vol. 335, No. 15., pp. 1150–1153.
Genotropin™ Brochure, Pharmacia & Upjohn, Inc., 1996, 9 pgs.
Cardizem® Lyo–Ject™ Brochure, 4 pgs. (No. 1.).
The Cardizem® (diltiazem HCl) Lyo–Ject™ Delivery System Brochure, 6 pgs.

*Primary Examiner*—Ronald Stright, Jr.
*Assistant Examiner*—A. T. Nguyen
*Attorney, Agent, or Firm*—Garvey, Smith, Nehrbass & Doody, L.L.C.

[57] ABSTRACT

A syringe apparatus includes a housing having upper and lower end portions and a hollow interior. A rotary cam position inside the hollow interior has a projecting portion for operating a cartridge when the apparatus is used. The housing has a rotary bearing for supporting the cam. A syringe cartridge (single chamber or dual chamber) removably fits the housing interior, the cartridge including a barrel with at least one chamber for containing medicine to be dispensed and a dispensing orifice. The cartridge includes a piston having an upper plunger that engages the cam. The piston slides within the barrel chamber forcing contained medicine through the dispensing orifice (e.g., needle) during use. The upper plunger end of the piston engages the rotary cam during dispensing. The cam is movable between first and second positions, the second position being a dispensing position that positions the projecting portion of the cam at the piston. A spring urges the cam to rotate from the first to the second position. A trigger is provided for engaging and holding the cam in the first position. The trigger can be activated to release the trigger and cam from engagement when in the first position so that the spring can move the cam from the first to the second position when the trigger is operated by a user. The needle automatically retracts after dispensing is complete.

16 Claims, 8 Drawing Sheets

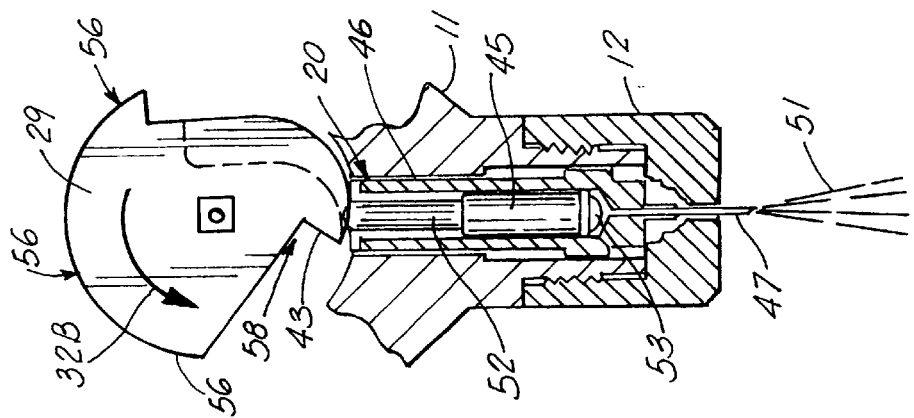
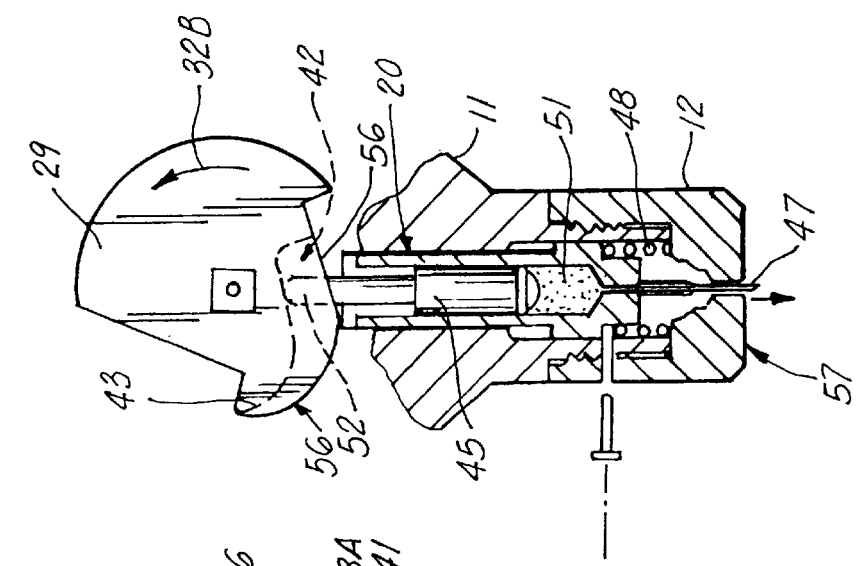
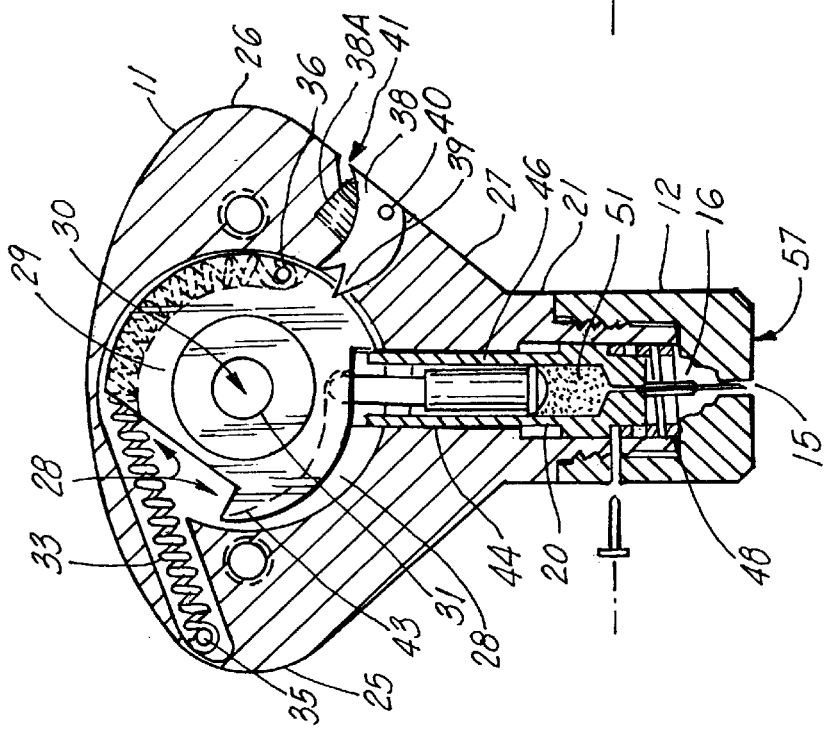

ROTARY CAM SYRINGE

BACKGROUND OF THE INVENTION:

1. Field of the Invention

The present invention relates to medical syringes and more particularly to an automatic rotary cam actuated syringe apparatus that can inject medicines and the like from removable cartridges (including single chamber and/or dual chamber syringes). Even more particularly, the present invention relates to an improved cam operated syringe that uses a cartridge that is pushed into a handle portion of the apparatus. The cam forces down and projects a needle, subsequently a plunger that ejects the medicine or drug, and wherein when the cam completes its rotation the inner barrel retracts so that the needle is no longer exposed.

2. General Background

Automatic syringes are used to administer parenteral medications to patients under emergency and routine situations. Urgent situations include, for example, military personnel who must administer analgesics, antibiotics or nerve gas antidotes under battlefield conditions. Persons who have severe allergies require immediate injections of epinephrine or glucocorticoids to prevent anaphylaxis. Sumatriptan or dihydroergotamine are frequently self-administered by migraineurs for immediate relief of headaches. Glucagon is often self-injected to counteract hypoglycemia in insulin dependent brittle diabetics.

Repetitive, non-urgent, use of automatic syringes is also common. Patients with chronic or prolonged medical conditions must often self-inject medications on a daily basis. Such injections include insulin by diabetics, low molecular weight heparin by patients predisposed to deep vein thrombosis, menotropins by infertile patients, growth hormone by short statured children, interferon beta-1a for multiple sclerosis, glucocerebrosidase-β-glucosidase for Gaucher's Disease and numerous other injectable drugs for anti-cancer therapy, analgesia and male erectile dysfunction.

While self-injection therapies are cost effective, many patients do not initiate such treatments. The most common reason self-injection with an automatic syringe is not widely accepted is needle phobia. An estimated 10% to 27% of the population have an unfounded fear of hypodermic needles. In such persons, fear and avoidance behavior is triggered by visual exposure to the needle. It is known that needle phobia can be minimized or overcome by hiding the needle before, during and after the injection procedure.

Various types of automatic syringes for administering parenteral medications are known. In my prior art U.S. Pat. No. 5,267,963, there is disclosed a cam operated syringe that has a transversely extended upper end housing, a sliding cam member that is spring loaded to first expose the syringe needle and then dispense the syringe contents. While my former patent provides for a hidden needle to penetrate, inject medication and retract the needle, it does not provide for a more compact design of a rotary cam nor for removal and replacement of a spent medication syringe. There is no concept for reactivating the device for repeat use.

Other automatic syringes have additional problems. Specifically, all reusable automatic syringe devices require the medication containing cartridge to be completely enclosed into the device, remounted with a cover, needle uncapped and other nuances before repeat use. For example, the recently released automatic syringe, Genotropin™, requires a total of twenty-three steps to remove a spent syringe cartridge, reload and automatically inject another medication. Such problems make home injection therapy particularly difficult in older patients who may be inept, possess manual tremors, have a loss in manual dexterity or possess other physical impairments. Another problem facing the user of a syringe is that of contamination. Contamination can in fact be in the form of a disease communicated from a patient to a doctor or a nurse if a syringe is contaminated and then carelessly handled. Needle recapping, or other accidental needle stick injury by persons exposed to contaminated needles from hepatitis or AIDS patients can have serious legal and life threatening consequences.

What is needed is a compact automatic syringe that will eliminate accidental contaminated needle stick injuries, overcome needle phobia, and remain user friendly by it's simplicity of use. In view of the foregoing, increased use of home health care for cost containment, and increasing use of bioengineered recombinant DNA drugs that are proteins and must be administered by injection, there is a need for a simple, re-usable and affordable automatic syringe.

Publications that discuss the problems of needlestick include, for example, THE JOURNAL OF FAMILY PRACTICE, Vol. 1, No. 2 (August) 1995, entitled "Needle Phobia: A Neglected Diagnosis", and THE JOURNAL OF AMERICAN MEDICAL ASSOCIATION, Aug./24/31, 1994 (Vol. 272, No. 8), entitled "Device-Specific Risk of Needlestick Injury in Italian Health Care Workers". THE NEW ENGLAND JOURNAL OF MEDICINE reports that the risk of percutaneous injury to health care workers causes these health care workers in the United States to receive approximately 800,000 needlesticks and related injuries from sharp objects annually. An estimated 16,000 of these devices are contaminated with human immunodeficiency virus, and even more are contaminated with hepatitis B virus or hepatitis C virus.

SUMMARY OF THE INVENTION

The present invention provides a safe, rotary cam operated syringe apparatus that includes a body with a handle for enabling a user to grip the apparatus. A cartridge is received into an interior portion of the body. As each cartridge is used, it is replaced with another.

With the present invention, a cam is released with a trigger. The entire inner barrel portion of the cartridge moves down to the distal end of the apparatus to expose a needle a predetermined distance below the body. As the cam continues to rotate, a plunger is then forced down, ejecting the contained medicine or preparation. While the present invention relates to injections into any body tissue and to any depth, the preferred embodiment relates to either subcutaneous or intramuscular injections ranging ¼ inch to 1½ inches below the body skin surface.

When the cam completes its rotation, the inner barrel retracts so that the needle is no longer exposed. Once the apparatus fires, it can't be reloaded until the original and now spent cartridge is removed.

The present invention thus provides an improved syringe apparatus that includes a housing having upper and lower end portions and a hollow interior. A rotary cam is positioned inside the hollow interior, the cam having projecting portions.

The housing has a rotary bearing for supporting the cam. A selected syringe cartridge (single or dual chamber) removably fits the housing interior. The cartridge includes a barrel with at least one chamber for containing medicine to be dispensed and a dispensing orifice that can include a hypodermic needle.

In one embodiment, the cartridge is a dual chamber syringe having two chambers that respectively include a dry medicinal component and a liquid component that can be mixed and/or reconstituted at the time that the drug or preparation is to be administered to a patient.

The cartridge includes a piston that slides within a barrel for forcing the contained medicine through a dispensing orifice. The upper end of the piston is in the form of a plunger that engages a groove on the rotary cam.

A spring urges the cam to rotate from a beginning position to a final position. A trigger engages and holds the cam in the initial position prior to use. When the trigger is activated, it releases the trigger and cam from engagement with one another when they are in the initial position so that the spring can move the cam from the initial to the final position.

The cam is so designed that the spent cartridge must be removed before the cam can be returned to the initial, spring loaded position.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 2 is a sectional elevational view of the preferred embodiment of the apparatus of the present invention showing the cam in the initial position before firing;

FIG. 3 is a sectional elevations view of the preferred embodiment of the apparatus of the present invention illustrating a second position of the cam when exposing the needle to enter a selected location on a patient;

FIG. 4 is a sectional elevational view of the preferred embodiment of the apparatus of the present invention illustrating a third position of the cam when dispensing of the contents of the cartridge;

Figure 1:
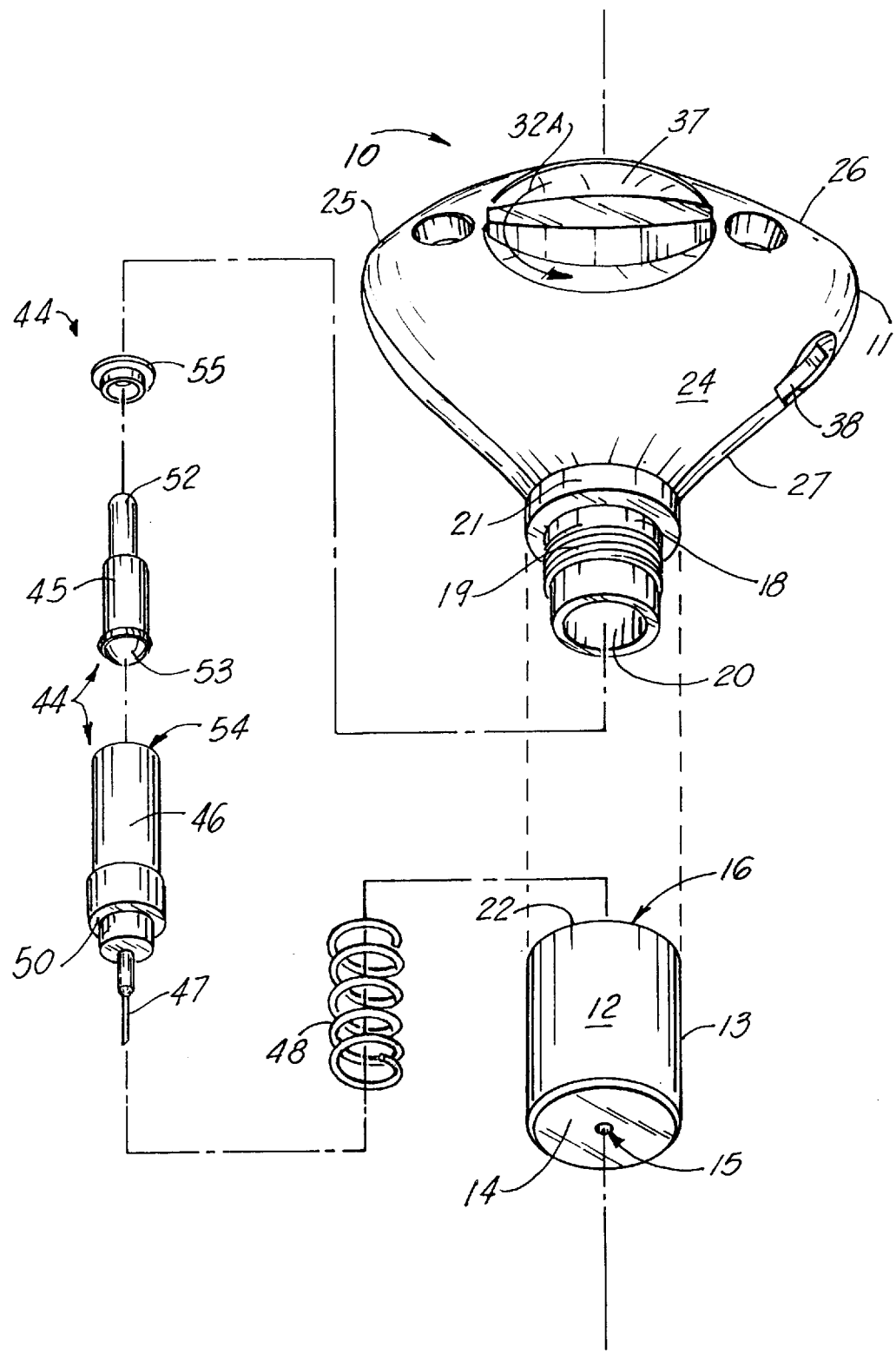
FIG. 1 is an exploded perspective view of the preferred embodiment of the apparatus of the present invention.

DETAILED DESCRIPTION OF THE PREFERRED EMBODIMENT:

FIGS. 1, 2 and 3 show generally the preferred embodiment of the apparatus of the present invention designated generally by the numeral 10.

Rotary cam syringe apparatus 10 has a housing that includes upper housing section 11 and lower housing section 12. Upper housing section 11 is shaped to fit the palm of a user's hand. Lower housing 12 has a cylindrical wall section 13, circular end plate 14 and opening 15 through which a hypodermic needle extends during use. A cylindrically shaped socket 16 of lower housing section 12 provides an internal connection 17 (e.g. bayonet, threads, etc.) for connecting with corresponding portion on upper housing section 11. Upper housing section 11 has a cylindrical lower end portion 18 with an external connector (bayonet, threads, etc.) 19 thereon.

Figure 7:
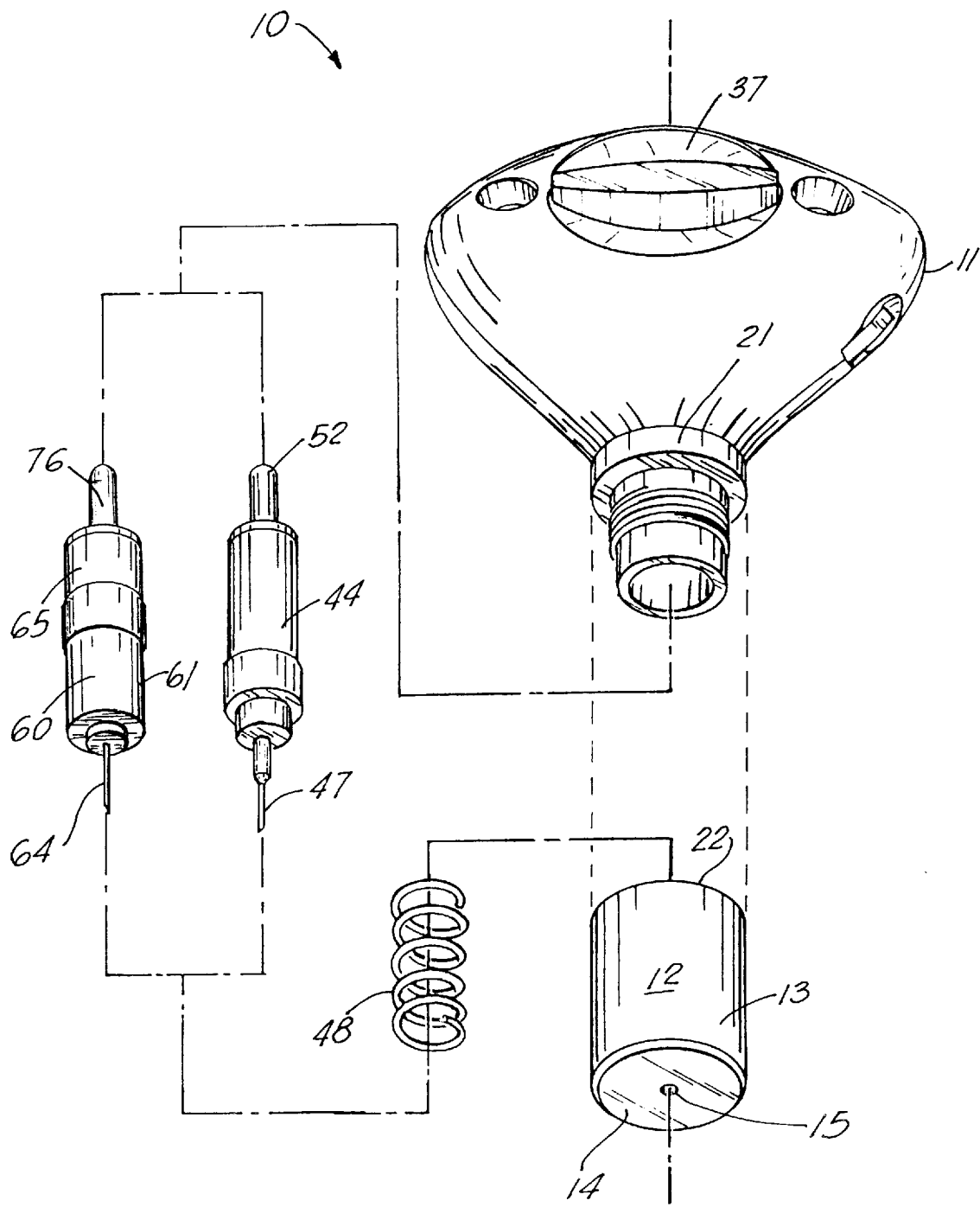
FIG. 7 is an exploded perspective view of the preferred embodiment of the apparatus of the present invention illustrating both single chamber and dual chamber cartridge portions thereof.

Upper housing section 11 has a cylindrically shaped socket 20 that receives a cartridge such as a single chamber cartridge 44 or a dual chamber cartridge 60 (see FIG. 7). Upon assembly, the upper end 22 of lower housing section 12 stops against annular shoulder 21 of upper housing section 11.

Upper housing section 11 is shaped to fit the palm of a user's hand, providing a gripping surface 24 that is generally convex with rounded side portions 25, 26. Upper housing section 11 also includes a generally conically shaped section 27 that extends from convex gripping surface 24 to annular shoulder 21 (FIGS. 1 and 2).

Upper housing section 11 is hollow, providing a hollow interior 28 that holds rotating cam 29. Rotating cam 29 rotates about axis of rotation 30 on rotary bearing 31. During use, rotating cam 29 moves from a first position as shown in FIG. 2 to a second position (FIG. 3), a third position (FIG. 4) and a fourth position (FIG. 5).

In the first position (FIG. 2), the user has loaded a fresh cartridge such as 44 or 60 into a cylindrically shaped cavity 20 that communicates with interior 28 of upper section 11. The cartridge 44 also extends into the socket 16 of lower section 12. Arrow 32B in FIG. 4 schematically illustrates the rotation of cam 29 from the first position of FIG. 2 to the second position of FIG. 3 to the third position of FIG. 4.

Figure 5:
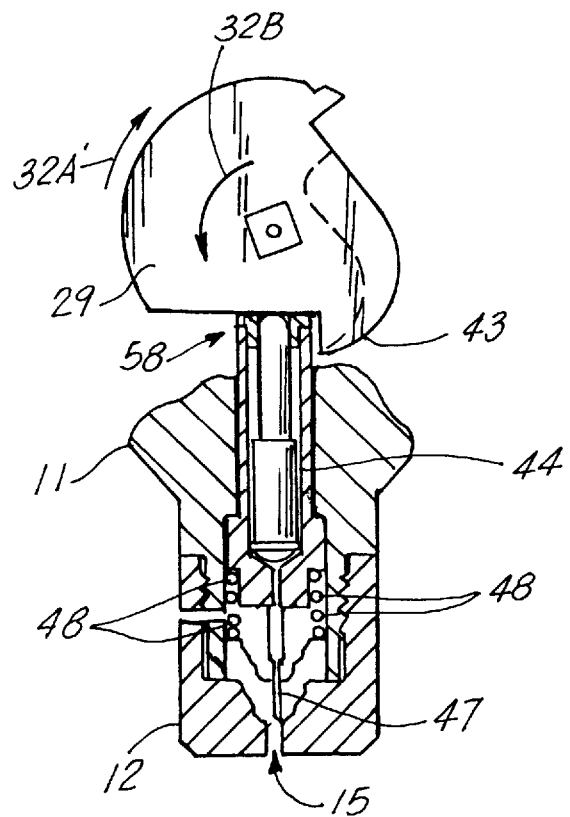
FIG. 5 is a sectional elevational view of the preferred embodiment of the apparatus of the present invention illustrating a fourth position of the cam when the needle is retracted.

A spring 33 urges cam 29 to travel from the first position of FIG. 2 to the fourth position of FIG. 5. In FIG. 2, spring 33 is extended, being fastened at its end portions to anchor pins 35 and 36. In order to load a cartridge 44 (or 60) into housing 11 at its cylindrically shaped chamber 20, the user removes any used or spent cartridge 44 (or 60) by separating housing sections 11 and 12.

The user rotates knob 37 in the direction of arrow 32A to spring load the cam 29. The cam 29 and knob 37 can be correspondingly keyed together for rotation when the user pushes knob 37 in a direction that forces knob 37 against the cam 29 and interlocks the cam 29 and knob 37. Once the cam 29 is rotated in the direction of arrow 32A, trigger 38 engages a recess on cam 29 and locks cam 29 in the first position of FIG. 2.

Trigger 38 is mounted upon pivot 40. Trigger 38 has a projecting end portion 39 that engages a correspondingly shaped recess on the outer most peripheral portion of rotating cam 29. Spring 38A urges trigger 38 into a locking position as shown in FIG. 2.

Figure 6:
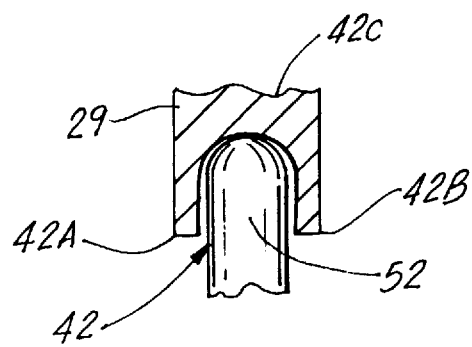
FIG. 6 is a fragmentary sectional view of the preferred embodiment of the apparatus of the present invention illustrating the cam and syringe plunger when in the first position of FIG. 2.

In FIG. 6, the user releases trigger 38 to rotate cam 29 by pressing the trigger 38 in the direction of arrow 41. This action overcomes the biasing force of spring 38A, releasing the projecting end portion 39 of trigger 38 from rotating cam 29. Once the trigger 38 has been released from its engagement with rotating cam 29, the spring 33 (which is extended in FIG. 2) rotates the cam 29 in the direction of arrow 32B so that the cam 29 moves toward the second position shown in FIG. 3.

As shown in FIG. 6, the rotating cam 29 has a U-shaped groove 42 that is shaped to conform to the upper plunger 52 end of piston 45. The rotating cam 29 has a pair of spaced apart shoulders 42A, 42B positioned on opposite sides of plunger 52 end of piston 44 as shown in FIG. 4.

When the trigger mechanism 38 is actuated by the user, the spring 33 moves the cam mechanism 29 from a first, loaded position to a second, unloaded position and in the process pushes the needle 47 to where it projects from the barrel 46 section (see FIG. 2), compresses the syringe plunger 52 to dispense a drug in the syringe cartridge 44, and retracts the needle 47 back into the lower housing section 12 through opening 15.

In FIG. 6, the cam 29 has a first cam surfaces 42A, 42B which engage the top surface of the syringe washer 55 so that the syringe cartridge 44 with needle 47 is pushed to the extended position shown in FIG. 2 as the cam mechanism 29 rotates toward the unloaded position, i.e., the top surface of the syringe washer 55 follows the first cam surfaces 42A, 42B. The cam mechanism 29 has a second cam 42C surface designed to interact with the syringe plunger 52 so that the syringe plunger 52 is compressed within the syringe 44 as the cam mechanism 29 rotates toward the unloaded position, i.e., the syringe plunger 52 follows the second cam surface 42C.

When the cam mechanism 29 moves from the loaded position to the unloaded position, the first cam surfaces 42A, 42B make contact with the top surface of the syringe washer 55 and thereafter the second cam surface 42C makes contact with the syringe plunger 52, respectively pushing each toward the position shown in FIG. 3. Cam surfaces 42A, 42B move needle 47 downwardly until it penetrates the patient's skin and travels into the underlying tissue.

With the shape of the first and second cam surfaces, the syringe barrel and syringe plunger travel in sync with each other until the needle has penetrated the skin to a desired depth. At this point, the second cam surface 42C operates to push the syringe plunger 52 at a faster rate than the first cam surfaces 42A, 42B are pushing the syringe barrel, such that the syringe plunger forces the drug contained in the syringe through the needle 47 as the needle 47 continues to penetrate the tissue a remaining distance of its travel to its final position (at a desired penetration depth of about 0.25 inches, as an example).

Retraction of the syringe back into the housing so that the needle is no longer exposed is accomplished by providing recess 58 which receives cartridge 44 as shown in FIG. 5. The construction of syringe cartridge 44 is shown in the exploded view of FIG. 1, and in FIGS. 2–5. Cartridge 44 includes a piston 45 having a smaller diameter upper plunger end 52 and a lower enlarged end 53. End 53 can be in the form of an annular rubber or like resilient member for forcing medicine from barrel section 46 of cartridge 44. Barrel 46 is provided with a central cylindrically shaped hollow bore 54 that corresponds in cross-section with the enlarged lower end 53 of piston 45. In this fashion, when the piston 45 moves downwardly within bore 54 of barrel 46, the contents 51 of bore 54 are discharged through hypodermic needle 47 that communicates with the medicine containing bore 54.

Barrel 46 has an annular shoulder 50 sized and shaped to receive coil spring 48. As shown in FIGS. 2 and 3, the coil spring 48 engages at its upper end, annular shoulder 50 at its upper end. At its lower end spring 48 engages circular end plate 14 of lower housing section 12. During use, the user first rotates the cam 29 to the position of FIG. 2. This locks the trigger 38 with the rotating cam 29 and allows the user to remove the lower section 12 of the housing so that a new cartridge 44 (or 60) can be added.

When a new cartridge 44 (or 60) is added, the spring 48 is slightly compressed to fully secure the cartridge 44 within the cylindrical chamber 20 section of hollow interior 28. This places an uppermost washer 55 of barrel 46 in the first position shown in FIG. 2.

When trigger 38 is depressed as shown by arrow 41 in FIG. 2, the cam 29 begins to rotate. The camming surface 56 gradually increases in radius with respect to center of rotation 30. This rotation initially compresses spring 48 projecting a small portion of hypodermic needle 47 beyond the flat face 57 portion of lower housing 12 as shown in the second position of FIG. 3.

In FIG. 4, a third position is reached wherein continued rotation in the direction of arrow 32B results in a complete compression of spring 48. In FIG. 4, the cam projecting end 43 and the ever increasing radial dimension of camming surface 56 results in a movement of plunger 52 and piston 45 downwardly to expel the medicine content 51 from chamber 54 of barrel 46.

Continued rotation of the rotating cam 29 places the plunger 52 at notch 58 and beyond projecting portion 43. However, this fourth position of FIG. 5 only occurs after all of the medicine has been dispensed from cartridge 44.

In the fourth position of FIG. 5, the plunger 52 reaches the recess 58 and spring 48 pushes cartridge 44 upwardly so that hypodermic needle 47 retracts within orifice 15. This prevents the user from being injured by the used hypodermic needle 47 of spent cartridge 44. The recess 58 also prevents rotation of the rotating cam 29 in the direction of arrow 32A until the spent cartridge 44 is removed. Once the lower housing section 12 has been disassembled from upper housing section 11 and cartridge and spent cartridge 44 removed, another cartridge 44 or 60 can be put into upper housing 11 and the process repeated.

In FIGS. 8–12, a dual chamber syringe cartridge 60 is shown. Dual chamber syringe cartridge 60 includes a lower section 61, upper section 65, floating piston 68, upper piston 73, and washer 78. The lower section 61 has a cylindrically shaped chamber 62 for containing a first component to be dispensed that can be for example a dry component. Lower section 61 has external threads 63 that form a connection with internal threads 67 of upper section 65. Lower section 61 can have a dispensing orifice such as hypodermic needle 64 for dispensing the contents of chamber 62.

Upper section 65 includes an open ended cylindrical bore 66 that can receive floating piston 68 and upper piston 73 during use. Floating piston 68 has circular ends 69, 70, a cylindrical side wall 71 and a pair of spaced apart annular O-rings 72.

Figure 8:
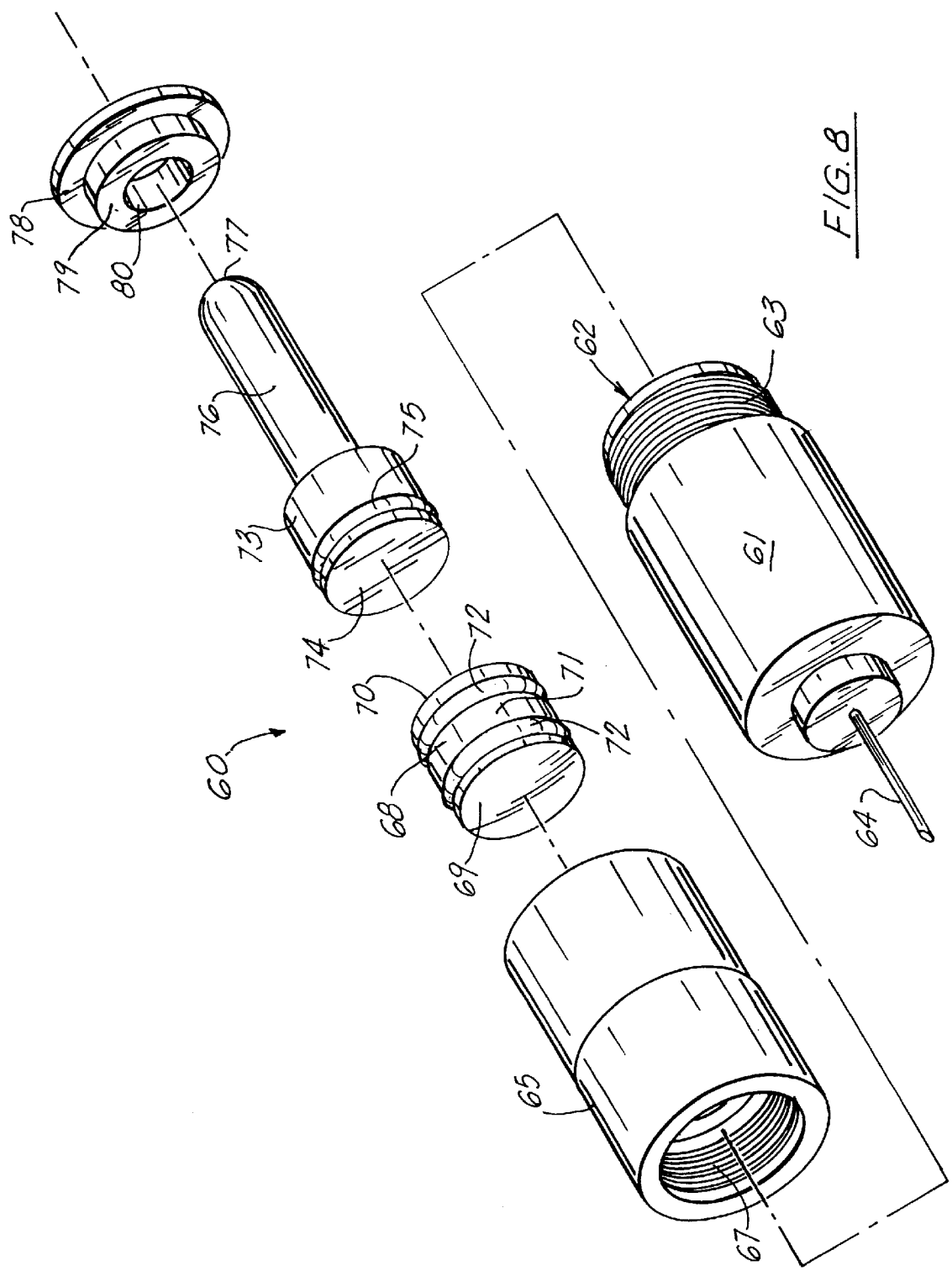
FIG. 8 is an exploded perspective view of a dual chamber cartridge that could be used with the preferred embodiment of the apparatus of the present invention.
Figure 9:
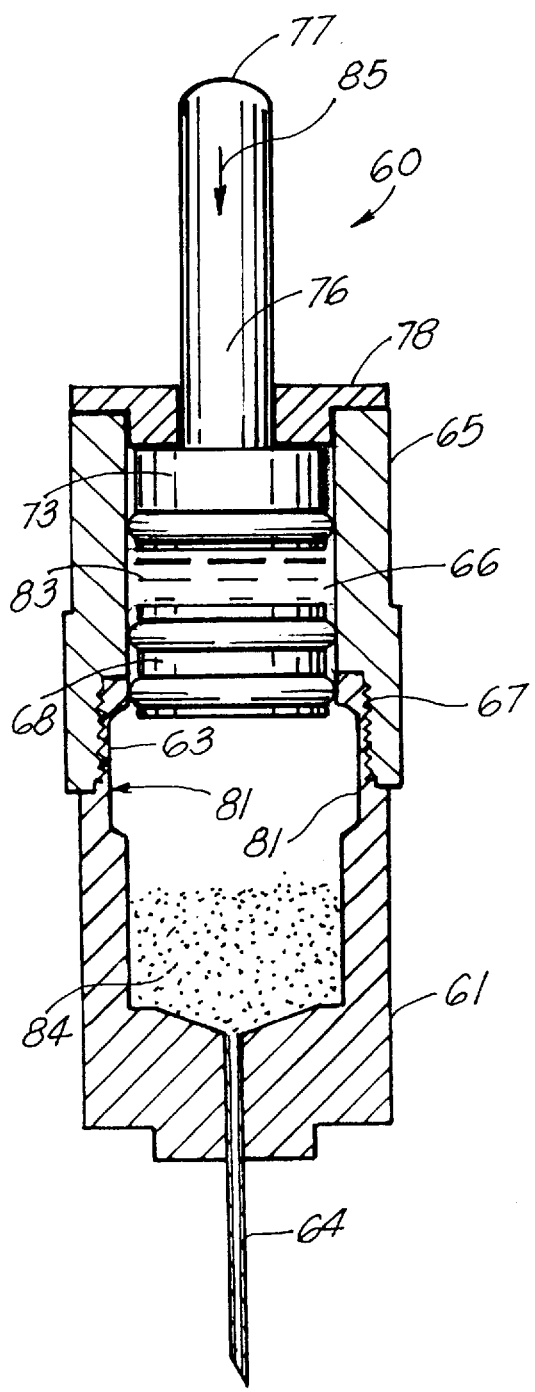
FIG. 9 is a sectional elevational view of the second embodiment of the apparatus of the present invention with the piston in the initial position prior to use.
Figure 10:
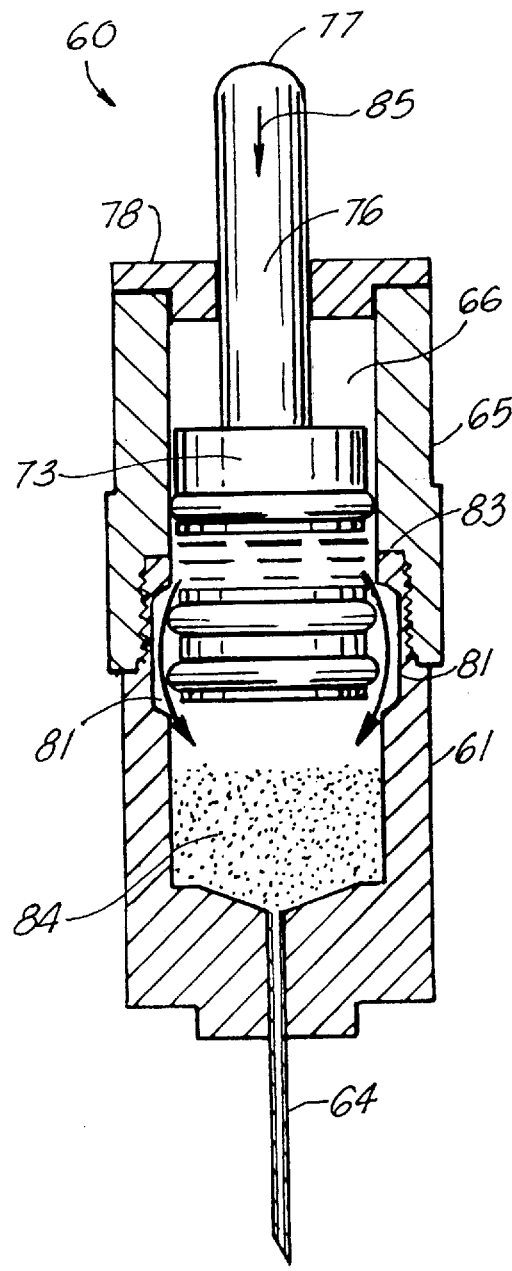
FIG. 10 is a sectional elevational view of the second embodiment of the apparatus of the present invention showing initial mixing of liquid and dry components as the piston moves downwardly.
Figure 11:
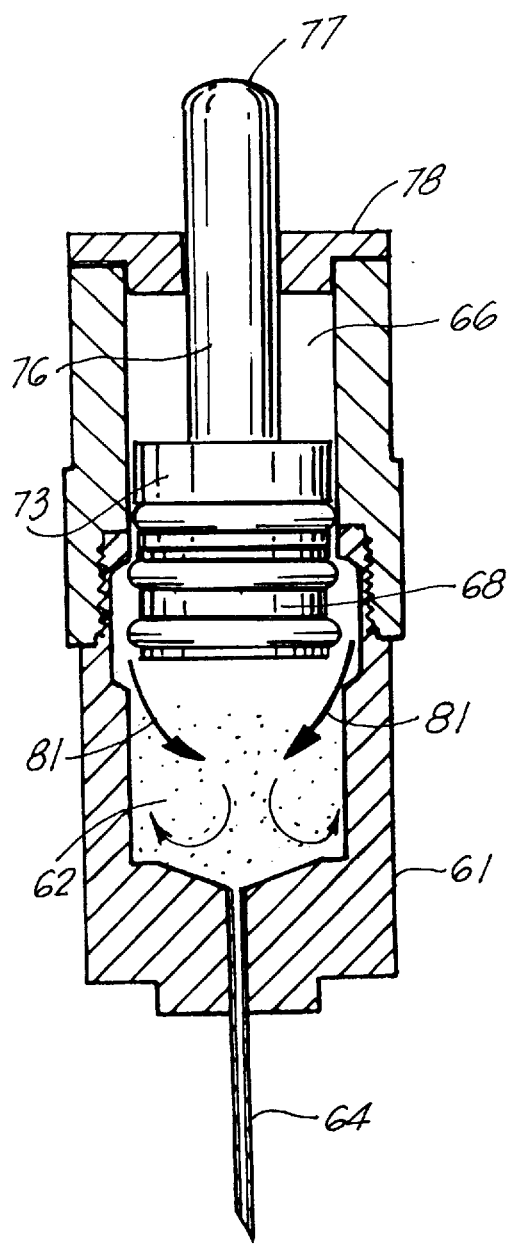
FIG. 11 is a sectional elevational view of the second embodiment of the apparatus of the present invention showing a position of the pistons after the liquid component has fully entered the lower chamber to mix with the dry component.
Figure 12:
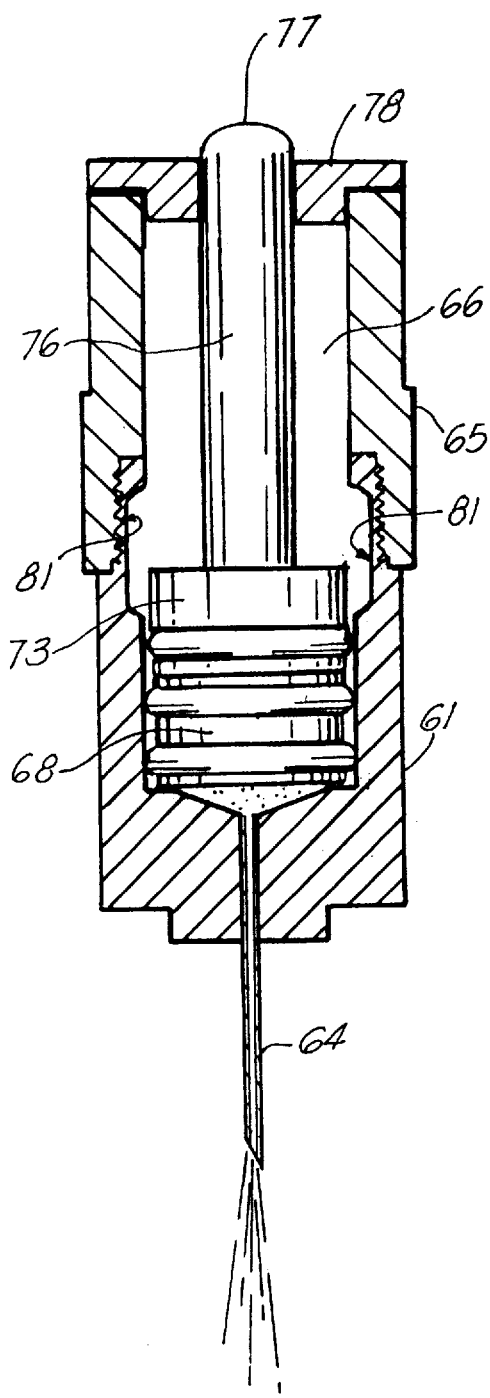
FIG. 12 is a sectional elevational view of the second embodiment of the apparatus of the present invention illustrating full travel of the pistons to the dispensing position wherein the liquid and dry components have mixed and been dispensed.

Upper piston 73 includes a circular end 74, O-ring 75, plunger 76 and upper end 77. During use, the rotary cam 29 engages the upper end 77 of plunger 76. Washer 78 forms a closure over the uppermost end of upper section 65 as shown in FIGS. 7 and 8. Washer 78 has an annular shoulder portion 79 and a cylindrical opening 80 that accommodates plunger 76.

A plurality of longitudinally extending and circumferentially shaped apart channels 81 are provided in lower housing 65 as shown in FIGS. 9–12. While one channel 81 could be provided, a plurality of channels 81 are preferred. In FIGS. 9–12, at least two channels are indicated for conveying fluid around floating piston 68 when plunger 76 is pushed downwardly in the direction of arrow 85. This causes a commingling of a liquid component 83 and dry component 84 in a reconstituting of the dry component to provide a reconstituted medicine or drug for administration to the patient. After mixing, continued downward movement of the plunger 76 in the direction of arrow 85 forces a reconstituted medicine or drug product through hypodermic needle 64. During the method shown in FIGS. 9–12, the user would typically invert the entire apparatus 10 so that the needle 64 is in the highest position to expel any air that is unwanted during the mixing or reconstituting.

Figure 13:
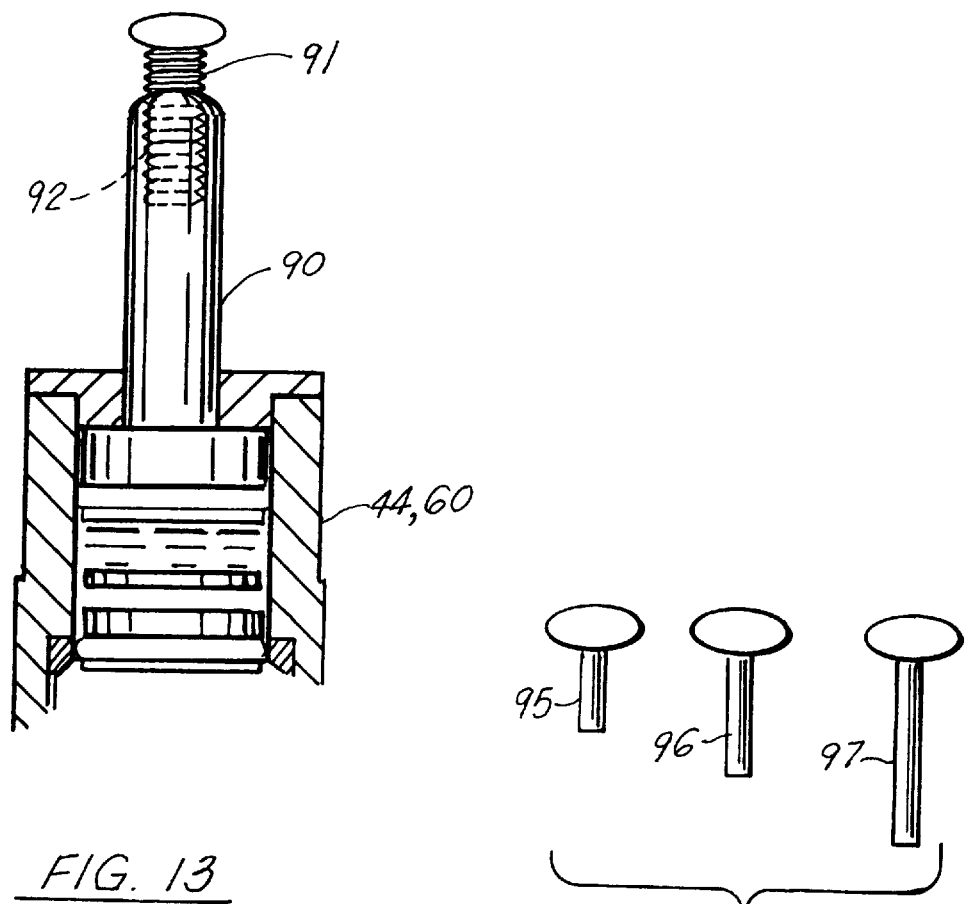
FIGS. 13–14 are sectional elevational views of adjustable plunger configurations that can be used with the present invention.
Figure 14:
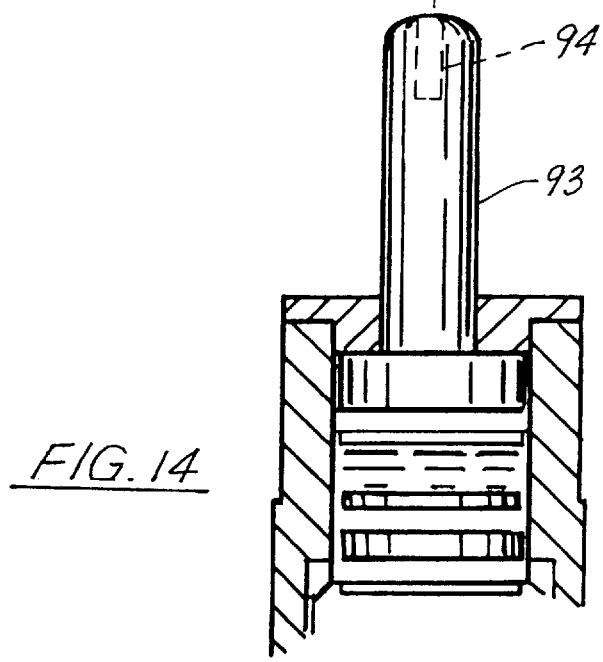

FIGS. 13–14 show two plunger configurations that can be used to vary the dosage of a selected cartridge 44 or 60. In FIG. 13, plunger 90 has an adjustable screw 91 as the plunger head. The adjustable screw plunger head 91 can be threaded externally to fit an internally threaded bore 92 of plunger 90. The cartridge 44 (or a dual chamber cartridge 60) can be used with plunger 90.

In FIG. 14, plunger 93 has a cylindrically shaped socket 94 that can accept plunger heads 95, 96, 97 that vary in length. Each plunger head fits socket 94. However, the dosage is varied depending upon the length plunger head 95, 96, 97 selected. The cartridge 44 (or a dual chamber cartridge 60) can be used with plunger 60.

The following table lists the parts numbers and parts descriptions as used herein and in the drawings attached hereto.

| PARTS LIST | |
|---|---|
| Part Number | Description |
| 10 | rotary cam syringe apparatus |
| 12 | lower housing |
| 13 | cylindrical wall |
| 14 | circular end plate |
| 15 | opening |
| 16 | socket |
| 17 | internal threads |
| 18 | cylindrical lower end |
| 19 | external threads |
| 20 | cylindrical socket |
| 21 | annular shoulder |
| 22 | upper end |
| 23 | enlarged upper end |
| 24 | gripping surface |
| 25 | rounded side |
| 26 | rounded side |
| 27 | conical section |
| 28 | hollow interior |
| 29 | rotary cam |
| 30 | axis of rotation |
| 31 | rotary bearing |
| 32A | arrow |
| 32B | arrow |
| 33 | spring |
| 34 | cylindrical channel |
| 35 | anchor pin |
| 36 | anchor pin |

-continued

| PARTS LIST | |
|---|---|
| Part Number | Description |
| 37 | knob |
| 38 | trigger |
| 39 | recess |
| 40 | pivot |
| 41 | arrow |
| 42 | groove |
| 42A | surface |
| 42B | surface |
| 42C | surface |
| 43 | projecting portion |
| 44 | syringe cartridge |
| 45 | piston |
| 46 | barrel |
| 47 | needle |
| 48 | coil spring |
| 49 | annular washer |
| 50 | annular shoulder |
| 51 | contents |
| 52 | upper end piston |
| 53 | enlarged lower end |
| 54 | bore |
| 55 | upper end |
| 56 | camming surface |
| 57 | face |
| 58 | V-shaped notch |
| 59 | |
| 60 | dual chamber syringe cartridge |
| 61 | lower section |
| 62 | cylindrical chamber |
| 63 | external threads |
| 64 | hypodermic needle |
| 65 | upper section |
| 66 | cylindrical bore |
| 67 | internal threads |
| 68 | floating piston |
| 69 | circular end |
| 70 | circular end |
| 71 | cylindrical side wall |
| 72 | O-ring |
| 73 | upper piston |
| 74 | circular end |
| 75 | O-ring |
| 76 | plunger |
| 77 | upper end |
| 78 | washer |
| 79 | annular shoulder |
| 80 | cylindrical opening |
| 81 | channels |
| 82 | arrows |
| 83 | liquid component |
| 84 | dry medicine |
| 85 | arrow |
| 90 | plunger |
| 91 | adjustable screw plunger head |
| 92 | threaded bore |
| 93 | plunger |
| 94 | socket |
| 95 | plunger head |
| 96 | plunger head |
| 97 | plunger head |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A syringe apparatus comprising:

a) a housing having upper and lower end portions and a hollow interior;

b) a cam positioned inside the hollow interior, the cam having a curved camming surface and a projecting portion;

c) the housing having a rotary bearing for supporting the cam;

d) a syringe cartridge that removably fits the housing interior, the cartridge including a barrel with at least one chamber for containing medicine to be dispensed, and a dispensing orifice;

e) the cartridge including a piston that slides within the barrel chamber for forcing the contained medicine through the dispensing orifice;

f) wherein an of the piston engages the rotary cam;

g) wherein the cam is rotational between first and second positions, the second position being a dispensing position that positions the projecting portion of the cam at the piston;

h) a spring for urging the cam to rotate from the first to the second position;

i) a trigger for engaging and holding the cam in the first position; and j) wherein the trigger can be activated to release the trigger and cam from engagement when in the first position so that the spring can move the cam from the first to the second position.

2. The syringe of claim 1 wherein the cartridge is a disposable container separable from the housing.

3. The syringe of claim 1 wherein the cartridge has two chambers for containing two separate medicinal portions.

4. The syringe of claim 3 wherein the cartridge has two pistons.

5. The syringe of claim 1 wherein the cam is a rotating cam that has a gradually increasing diameter curved camming portion.

6. The syringe of claim 1 further comprising a handle that extends from the housing for enabling a user to move the cam from the second to the first position.

7. The syringe of claim 6 wherein the trigger engages the cam when the cam is rotated from the second to the first position.

8. The syringe of claim 1 wherein the housing includes upper and lower sections that are connectable.

9. The syringe of claim 8 wherein the upper and lower sections separate to enable removal and insertion of syringe cartridges.

10. The syringe of claim 8 wherein the upper and lower sections are removably engaged.

11. The syringe of claim 1 wherein the housing has a needle opening and the cartridge dispensing outlet includes a needle that extends through the housing opening during use.

12. The syringe of claim 1 wherein the rotary cam has a grooved portion that receives an upper end of the piston during movement of the cam from the first to the second position.

13. The syringe of claim 12 further comprising a pair of shoulders at the groove that track respective sides of the piston during use.

14. The syringe of claim 12 wherein the groove is U-shaped.

15. The syringe of claim 14 wherein the upper end of the piston closely fits the U-shaped groove.

16. The syringe of claim 1 further comprising a syringe spring for holding the piston in an upper position, wherein the cam spring overcomes the piston spring during dispensing.

* * * * *